(12) United States Patent
Mizutani et al.

(10) Patent No.: US 7,367,966 B2
(45) Date of Patent: May 6, 2008

(54) INTERLABIAL PAD

(75) Inventors: Satoshi Mizutani, Kagawa (JP); Koichi Yamaki, Kagawa (JP); Yuki Noda, Kagawa (JP); Megumi Tokumoto, Kagawa (JP); Akane Sakai, Kagawa (JP)

(73) Assignee: Uni-Charm Corporation, Kawanoe-Shi, Ehime (JP)

( * ) Notice: Subject to any disclaimer, the term of this patent is extended or adjusted under 35 U.S.C. 154(b) by 104 days.

(21) Appl. No.: 10/705,407

(22) Filed: Nov. 10, 2003

(65) Prior Publication Data
US 2004/0158220 A1    Aug. 12, 2004

Related U.S. Application Data

(63) Continuation of application No. PCT/JP02/04888, filed on May 21, 2002.

(30) Foreign Application Priority Data

May 22, 2001   (JP)   ............... 2001-152403
Mar. 6, 2002   (JP)   ............... 2002-059860

(51) Int. Cl.
    *A61F 13/15*   (2006.01)
(52) U.S. Cl. ............... 604/385.17; 604/385.01; 604/384; 604/385.03; 604/386
(58) Field of Classification Search ......... 604/385.17, 604/385.18, 385.01, 11–18, 385.02, 384, 604/385.03, 386, 385.04, 904; D24/141
See application file for complete search history.

(56) References Cited

U.S. PATENT DOCUMENTS

| 4,595,392 | A | * | 6/1986 | Johnson et al. | ........ 604/385.17 |
| 5,057,096 | A |   | 10/1991 | Faglione | |
| 5,618,282 | A | * | 4/1997 | Schlangen | ........ 604/387 |
| 6,332,878 | B1 | * | 12/2001 | Wray et al. | ........ 604/328 |

FOREIGN PATENT DOCUMENTS

CN   1027039 A1   12/1994
CN   1190883 A1    8/1998

(Continued)

OTHER PUBLICATIONS

Mizutani, et al., "Flap-Equipped Interlabial Pad", U.S. Appl. No. 10/705,670, Nov. 10, 2003.

(Continued)

*Primary Examiner*—Jacqueline F. Stephens
(74) *Attorney, Agent, or Firm*—Darby & Darby P.C.

(57) ABSTRACT

The present invention relates to an interlabial pad that is worn by female wearers, placed in intimate contact and supported between the labia, which provides an interlabial pad that gives no discomfort to the female wearer in the body motions of the wearer.

The interlabial pad of the present invention is characterized by having a structure and/or shape which allows the pad to make right and left phase shifts easily, even when a shearing force is exerted on the interlabial pad by the wearer's body motion, that is, a structure and/or shape which reduces the friction.

17 Claims, 11 Drawing Sheets

FOREIGN PATENT DOCUMENTS

| | | |
|---|---|---|
| CN | 1268040 A | 9/2000 |
| EP | 1 018 328 A1 | 7/2000 |
| EP | 1 097 065 A1 | 5/2001 |
| EP | 1 097 685 A2 | 5/2001 |
| JP | 54-168797 A1 | 11/1979 |
| JP | 4-128729 A1 | 11/1992 |
| JP | 5-18523 A1 | 3/1993 |
| JP | 6-506368 A1 | 7/1994 |
| JP | 10-33589 A1 | 2/1998 |
| JP | 11-009623 A | 1/1999 |
| JP | 11-104167 A1 | 4/1999 |
| JP | 11-138673 A | 5/1999 |
| JP | 11-291376 A1 | 10/1999 |
| JP | 11-332793 A1 | 12/1999 |
| JP | 2000-42090 A1 | 2/2000 |
| JP | 2001-506168 A1 | 5/2001 |
| JP | 2001-507597 A1 | 6/2001 |
| TW | 2819 A1 | 3/1955 |
| TW | 234688 A1 | 11/1994 |
| TW | 247431 A1 | 5/1995 |
| TW | 247463 A1 | 5/1995 |
| TW | 294591 A1 | 1/1997 |
| TW | 316443 A1 | 9/1997 |
| TW | 338315 A1 | 8/1998 |
| TW | 354481 A1 | 3/1999 |
| TW | 362966 A1 | 7/1999 |
| TW | 374720 A1 | 11/1999 |
| TW | 386030 A1 | 4/2000 |
| TW | 386872 | 4/2000 |
| TW | 386872 A1 | 4/2000 |
| TW | 386873 A1 | 4/2000 |
| TW | 388711 A1 | 5/2000 |
| TW | 394681 A1 | 6/2000 |
| TW | 416847 A1 | 1/2001 |
| TW | 442278 A1 | 6/2001 |
| TW | 450802 A1 | 8/2001 |
| TW | 454503 A1 | 9/2001 |
| TW | 470640 A1 | 1/2002 |
| TW | 524677 A1 | 3/2003 |
| WO | WO-94/17115 A1 | 8/1994 |
| WO | WO-95/31165 A1 | 11/1995 |
| WO | WO-98/08475 A1 | 3/1998 |
| WO | WO-98/25561 A1 | 6/1998 |
| WO | WO-98/29078 A1 | 7/1998 |
| WO | WO-98/57610 A1 | 12/1998 |
| WO | WO-99/01093 A1 | 1/1999 |
| WO | WO-99/01096 A1 | 1/1999 |
| WO | WO-99/25295 A1 | 5/1999 |
| WO | WO-99/26575 A1 | 6/1999 |
| WO | WO-99/55270 | 11/1999 |
| WO | WO-99/56689 A1 | 11/1999 |
| WO | WO-55272 A1 | 11/1999 |

OTHER PUBLICATIONS

Mizutani, et al., "Interlabial Pad and Package Thereof", U.S. Appl. No. 10/705,810, Nov. 10, 2003.
Mizutani, et al., "Interlabial Pad", U.S. Appl. No. 10/705,406, Nov. 10, 2003.
Mizutani, Satoshi, "Interlabial Product Having Form for Finger Securement, and Individual Package", U.S. Appl. No. 10/705,779, Nov. 10, 2003.
Mizutani, et al., "Interlabial Pad", U.S. Appl. No. 10/705,408, Nov. 10, 2003.
Mizutani, et al., "Interlabial Pad Individual Packaging Vessel", U.S. Appl. No. 10/705,673, Nov. 10, 2003.
Mizutani, et al., "Interlabial Pad", U.S. Appl. No. 10/705,780, Nov. 10, 2003.
Mizutani, et al., "Interlabial Pad", U.S. Appl. No. 10/705,778, Nov. 10, 2003.
Mizutani, et al., "Interlabial Pad and Package Thereof", U.S. Appl. No. 10/705,404, Nov. 10, 2003.
Mizutani, et al., "Interlabial Pad and Package Thereof", U.S. Appl. No. 10/705,400, Nov. 10, 2003.
Mizutani, et al, "Interlabial Pad and Package", U.S. Appl. No. 10/706,303, Nov. 10, 2003.
Mizutani, et al., "Interlabial Pad Individual Packaging Body", U.S. Appl. No. 10/705,669, Nov. 10, 2003.
Mizutani, et al., "Interlabial Pad", U.S. 10/705,811, Nov. 10, 2003.
Mizutani, et al., "Interlabial Pad", U.S. Appl. No. 10/705,403, Nov. 10, 2003.
Mizutani, et al., "Interlabial Pad", U.S. Appl. No. 10/705,812, Nov. 10, 2003.
Mizutani, et al., "Individual Packaging Body and Outer Vessel Therefor", U.S. Appl. No. 10/705,402, Nov. 10, 2003.
Mizutani, et al., "Interlabial Pad", U.S. Appl. No. 10/705,399, Nov. 10, 2003.
Mizutani, et al., "Interlabial Pad Individual Packaging Vessel, and Individual Packaging Body", U.S. Appl. No. 10/705,781, Nov. 10, 2003.
Mizutani, et al., "Flap-Equipped Interlabial Pad", U.S. Appl. No. 10/705,670, Nov. 10, 2003.
Mizutani, et al., "Interlabial Pad and Package Thereof", U.S. Appl. No. 10/705,810, Nov. 10, 2003.
Mizutani, et al., "Interlabial Pad", U.S. Appl. No. 10/705,406, Nov. 10, 2003.
Mizutani, Satoshi, "Interlabial Product Having Form for Finger Securement, and Individual Package", U.S. Appl. No. 10/705,779, Nov. 10, 2003.
Mizutani, et al., "Interlabial Pad", U.S. Appl. No. 10/705,408, Nov. 10, 2003.
Mizutani, et al., "Interlabial Pad Individual Packaging Vessel", U.S. Appl. No. 10/705,673, Nov. 10, 2003.
Mizutani, et al., "Interlabial Pad", U.S. Appl. No. 10/705,780, Nov. 10, 2003.
Mizutani, et al., "Interlabial Pad", U.S. Appl. No. 10/705,778, Nov. 10, 2003.
Mizutani, et al., "Interlabial Pad and Package Thereof", U.S. Appl. No. 10/705,404, Nov. 10, 2003.
Mizutani, et al., "Interlabial Pad and Package Thereof", U.S. Appl. No. 10/705,400, Nov. 10, 2003.
Mizutani, et al., "Interlabial Pad and Package", U.S. Appl. No. 10/706,303, Nov. 10, 2003.
Mizutani, et al., "Interbial Pad Individual Packaging Body", U.S. Appl. No. 10/705,669, Nov. 10, 2003.
Mizutani, et al., "Interlabial Pad", U.S. Appl. No. 10/705,811, Nov. 10, 2003.
Mizutani, et al., "Interlabial Pad", U.S. Appl. No. 10/705,403, Nov. 10, 2003.
Mizutani, et al., "Interlabial Pad", U.S. Appl. No. 10/705,812, Nov. 10, 2003.
Mizutani, et al., "Individual Packaging Body and Outer Vessel Therefor", U.S. Appl. No. 10/705,402, Nov. 10, 2003.
Mizutani, et al., "Interlabial Pad", U.S. Appl. No. 10/705,399, Nov. 10, 2003.
Mizutani, et al., "Interlabial Pad Individual Packaging Vessel, and Individual Packaging Body", U.S. Appl. No. 10/705,781, Nov. 10, 2003.

\* cited by examiner

X1-X2 Cross Section (A)

(B)

INTERLABIAL PAD

CROSS-REFERENCE TO RELATED APPLICATIONS

This application is a Continuation of International Application No. PCT/JP02/04888 filed May 21, 2002, which application published in Japanese on Nov. 28, 2002 as WO 02/094152 A1 under PCT Article 21(2).

BACKGROUND OF THE INVENTION

1. Technical Field

The present invention relates to an interlabial pad that is able to be worn by female wearer, being placed in an intimate contact between the labia.

2. Background Art

Conventionally, a sanitary napkin and a tampon are used generally as a female sanitary products. Here, there have been great efforts to prevent the leak of menstrual blood from gap caused by a poor contact state near the ostium vaginae as for the sanitary napkin. Moreover, as for the tampon, there have been great efforts for relieving a foreign feeling and discomfort when wearing a tampon product and intervaginal wearing trouble due to the nature of those products.

Under such situation, a sanitary product of the interlabial pad have attracted people as a sanitary product positioned between the sanitary napkin and the tampon in recent years. The interlabial pad is used by inserting its portion between the labia and bringing into contact with a labia inner face, it prevents the menstrual blood from leaking since it has higher adhesion to the body than that of the sanitary napkin, and the menstrual blood from being diffused and brought widely into contact with the body, so it is sanitary and clean. Moreover, the interlabial pad which has characteristics that it excels in a wear feeling, is comfortable because of being smaller than the sanitary napkin, and has lower psychological resistance on wearing than that of the tampon which is inserted into the vagina.

Unlike a sanitary napkins being fixed to an underwear or a tampon and being fixed by insertion into the vagina, the interlabial pad is usually used and fixed to the body by inserting it between the labia, which may make right and left phase shifts in body motions. Therefore, it is necessary that the interlabial pad can make right and left phase shifts flexibly to follow the wearer's body motions. That is, it is required to the motions of the labia corresponding to the asymmetric body motions with respect to the body's longitudinal plane of symmetry, which extends along the anteroposterior axis, like putting one foot in front of the other alternately in walking. If the interlabial pad cannot follow the body motions and falls from the wearer's interlabial space, the resulting leak of menstrual blood is a significant problem. The "right and left phase shifts" refer to a broad concept including asymmetric or separate changes of the right and left sides (The change includes changing positions and moving.).

As a conventional example of such device, an absorbent interlabial device is disclosed (Japanese Patent Publication No. 2001-506168). The absorbent interlabial device comprises a liquid permeable topsheet, a liquid non permeable backsheet and an absorbent core positioned between the topsheet and backsheet. The length of the absorbent interlabial device is greater than about 60 mm and less than about 130 mm. The width of the device is between about 25 mm and about 50 mm. The device comprises an axis of preferred bending, located along the longitudinal centerline of the device. When the device is folded along this axis and is inserted into the wearer's interlabial space, the topsheet maintains contact with the walls of the wearer's labia.

When being inserted between the labia, the absorbent interlabial device is folded to be accommodated in the space. However, unlike a usual sanitary napkin, the interlabial pad is not fixed to the underwear or not fixed by insertion like a tampon. The interlabial pad is inserted between the labia in such condition that the pad may slip or shift and is not fixed as securely as the sanitary napkin or tampon. Therefore, with the wearer's body movement, slips between the absorbent interlabial device (equivalent to the interlabial pad) and the labia may tend to occur, which may make the wearer feel discomfort.

DISCLOSURE OF THE INVENTION

The present invention is directed to solve problems pointed out above. The object of the invention is, with the interlabial pad placed in intimate contact with and supported between labia, to reduce discomfort as much as possible which the wearer of the pad feels when some force is exerted on either the interlabial pad or the labia by the body motions.

The inventors found out that it might be the slip between the interlabial pad and inner walls of the labia or some force felt between the interlabial pad and the inner walls of the labia, even without any slips, which makes the wearer feel discomfort. Such force is apt to be produced by the wearer's asymmetric motions. For example, as for an interlabial pad which is worn by being folded, the left labium is to contact the left side of the interlabial pad and the right labium is to contact the right side of the interlabial pad. If the interlabial pad had enough flexibility, problems pointed above would not arise. Because the right and left sides of the folding line of the interlabial pad could make right and left phase shifts to some extent. However, in some cases, the friction between the back side sheet and itself contacting each other being caused by the right and left phase shifts in body motion makes it difficult to maintain the wearing position. For example, when an asymmetric motion, such as walking movement of the wearer, is made, the surfaces of the right and left sides of the interlabial pad contacting right and left labia, respectively, try to follow the asymmetric movement. However, the frictional force arising from the back side sheet makes it difficult for the right and left sides of the interlabial pad to make right and left phase shifts with respect to the folding line. This does not only cause a feeling of discomfort to the wearer but also results in that either or both surfaces of the right and left sides of the interlabial pad contacting left and right labia surfaces, respectively, come off from the labium. Consequently, the pad falls off the labia because its holding force is lost.

Additionally, when the frictional force between the back side sheet and the underwear becomes greater than the holding force of the labia to hold the interlabial pad, the pad can not follow the wearer's body motion, which not only causes a feeling of discomfort to the wearer but also raise the strong possibility that the interlabial pad may fall off the labia. Thus, achieving low friction between the back side sheet and itself, or between the back side sheet and another thing such as underwear, is clearly preferable. The inventors also found out that low friction could be achieved easily and effectively by contriving the surface shape of the back side sheet.

The present invention is developed based on the above-mentioned findings and provides an interlabial pad being fixed to labia in intimate contact with a structure and/or shape which allows flexible, asymmetric movements even when a shearing force is exerted on the interlabial pad by body motion, i.e., a structure and/or shape which achieves low friction.

More specifically, the present invention provides the following:

(1) An interlabial pad having a size, a weight and flexibility so as to be pinched and held partially or totally in between the labia without forcing, the pad comprising: a body side face orientated toward a body side, and an opposite side face to the body side face orientated toward a garment side and; wherein said opposite side face to the body side face has a surface shape ("low friction shape") of low resisting force by sliding with another face, which includes a same face.

"Partially or totally" may mean that a part or the whole of the interlabial pad is to be unseen by inserting the interlabial pad between labia. To be pinched without forcing may mean that the wearer who wears the interlabial pad inserts it between her labia without an unnatural force. To hold may mean that the pad should not fall from the place where it is inserted. The body side face oriented to the body side may have at least some portion thereof that is oriented toward the body side. The opposite body side face to the body side face may have at least some portion thereof that is oriented to the clothing side is not necessarily faced the side away from the body.

The "surface shape of the opposite body side face" refers to a shape which is located on the opposite side face to the body side face or retained by a member positioned on the opposite side face to the body side face. It is not necessary that the member or the opposite side face has to retain such shape over the whole member or the whole surface. But at least a part thereof may have such surface. "Same face" may mean the same face which is formed on the opposite side face or by a member located on the opposite side face to the body side and which is located at different places on the opposite side face. For example, the same face may refer to a different face (part) located on the same face of the part which comes into contact with the face by bending the surface.

"Another face" may include the same face mentioned above and surfaces of a different member, e.g., a surface formed on a clothing such as underwear.

"A surface shape of low resisting force by sliding ("low friction shape")" means a surface shape, that is, a low resistance shape when sliding with the same type of surface or a predetermined surface under a predetermined condition. And it is a shape other than surfaces having engaging portions such as a hook and loop (for example, MAGIC TAPE (Japanese registered trade mark)).

(2) The interlabial pad according to (1), wherein said low friction shape comprises a shape having a substantially small contact area between sliding two faces.

Here, "sliding two faces" may comprise one face referring to a face on the opposite side face to the body side face and the other face referring to a face located at other place on the same opposite side face or another face on a clothing or the like. The Substantial contact area may refer to the total area of portions, which actually contact each other, of the two surfaces that appear to contact each other. "Contact" may include contact via solid material or viscous fluid and may mean the state where one surface transmits a friction force to the other mating surface by sliding. More specifically, the shape having a substantially small contact area may be a shape of mating faces that have an actually small contact area.

(3) The interlabial pad according to (1) or (2), wherein said low friction shape comprises a group of fine convex shapes.

The "fine convex shape" may be a partially projected shape from a reference surface of the base face on the opposite side face to the body side face and it may be smaller than that of the base face on the opposite side face to the body side face. "A group of" may mean that the low friction shape comprises a plurality of convex shapes since only one convex shape may not form the low friction shape.

(4) The interlabial pad according to (3), wherein said fine convex shape is an emboss portion processed by an emboss former.

The "emboss portion processed" refers to a part which protrudes from the reference surface of the base face of the opposite side face to the body side face and particularly, to a part having a protrusion small enough in comparison to the base face of the opposite side face to the body side face. Seen from the above, a shape of the emboss portion protruding upward is usually a circle. However, the shape may be a rectangle, an ellipse or other shapes so that it is not limited to a circle.

(5) The interlabial pad according to (4), wherein an emboss rate of said fine convex shape is at least 1% and not exceeding 50%. The "emboss rate" is determined by dividing the total area of emboss portions by the total area on the opposite side face to the body side face which can be processed by the emboss former.

(6) The interlabial pad according to (1) or (2), wherein said low friction shape is made of a fiber assembly. The "fiber assembly" refers to plural fibers which are gathered to form a cluster. The fiber assembly includes woven fabrics and nonwoven fabrics.

(7) The interlabial pad according to (6), wherein said fiber assembly is made of nonwoven fabric.

The "nonwoven fabric" may refer to fabrics except woven fabrics and may include fabrics made by spun bonding, spun lacing, through air, needle punching and other methods.

(8) The interlabial pad according to any one from (1) to (7), wherein said opposite side face to the body side face is made of a low friction material.

The "low friction material" refers to materials including an inorganic material and an organic material such as polymers of polytetrafluoroethylene, and materials having a small frictional coefficient in a dry condition, materials having a low friction against fabrics including cloth made of fibers, nonwoven fabric, etc., materials having a low friction against themselves. The "small frictional coefficient" refers to a value of 0.3 or less, and more preferably, 0.1 or less.

(9) The interlabial pad according to any one from (1) to (8), wherein a lubricant is applied to said opposite side face to the body side face.

The lubricant refers to lubricants including solid lubricants, such as smooth powder, and fluid lubricants, such as silicone oil, which have particularly low toxicity and no health and sanitary problems.

(10) The interlabial pad according to any one from (1) to (9), wherein said interlabial pad comprises a mini sheet piece.

The "mini sheet piece" may refer to an attachment to the outside of said interlabial pad and may form a sac or bridge together with the interlabial pad.

(11) The interlabial pad according to any one from (1) to (10), wherein said interlabial pad is an interlabial pad for an incontinence.

According to the interlabial pad of the present invention, the pad can be used for incontinence absorbing pad. As ostium vaginae where the menstrual blood is discharged and a urethral meatus where urine is discharged are located between labia, and the interlabial pad of the invention to be used between the labia can absorb urine also.

As described hereinbefore, the pad of the invention can absorb urine between the labia, especially around the urethral meatus and is useful for the absorbing pad for incontinence, especially for a light incontinence.

(12) The interlabial pad according to any one from (1) to (10), wherein said interlabial pad is an interlabial pad for absorbing vaginal discharge.

In accordance with the present invention, the interlabial pad can be used for a pad of absorbing the vaginal discharge. The interlabial pad according to the present invention is used between the labia and can absorb the excretion other than the menstrual blood from the ostium vaginae for the use therefore (for absorbing the vaginal discharge).

As described above, the pad can absorb the vaginal discharge in order to decrease the discomfort for the wearer, and is useful for the wearer who is not menstruating.

(13) A method for reducing a foreign feeling of an interlabial pad wearer by using the interlabial pad of any one from (1) to (12).

With this method complaints of the interlabial pad wearer who wears an analogous but different interlabial pad and claims feelings of discomfort are resolved.

BEST MODE FOR CARRYING OUT THE INVENTION

Next, the embodiments of the interlabial pad according to the present invention will be described with reference to the figures.

Basic Interlabial Pad

Figure 1:
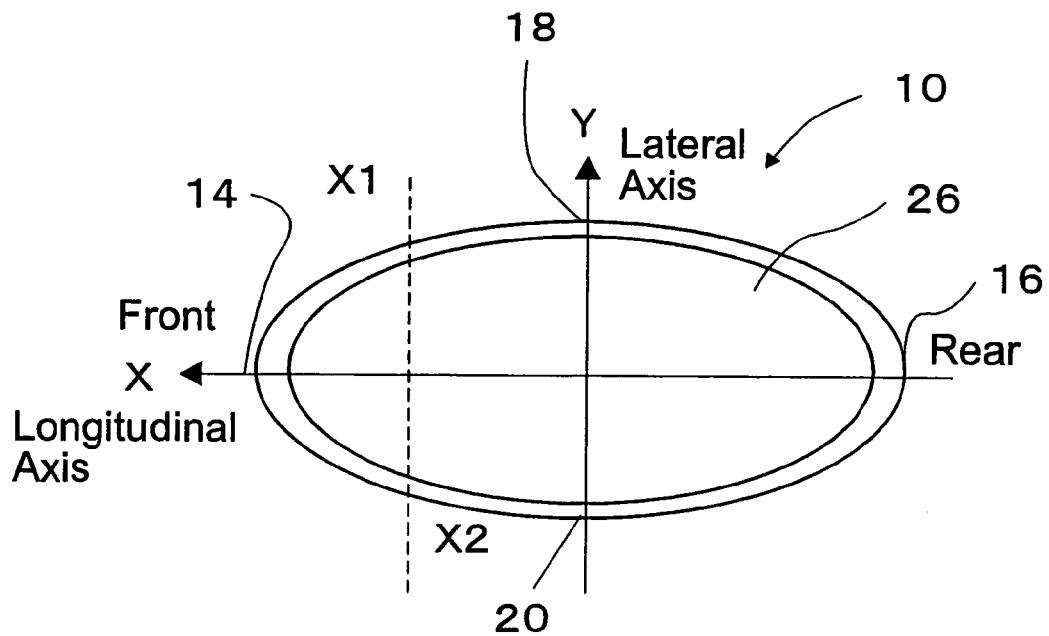
FIG. 1 is a plan view of an interlabial pad of the present embodiment seen from the body side face.

FIG. 1 shows a schematic plan view of an interlabial pad 10. An interlabial pad essentially has a shape which is elongated longitudinally, that is, an elliptical shape having the major axis from front 14 to rear 16 along the longitudinal axis (X-axis), and the minor axis from right 18 to left 20 on the lateral axis (Y-axis). However, the shape of the product is not necessarily limited to it, but it may be any one of the shapes which are suitable for the labial area and allow right and left phase shifts during use, such as an elliptical shape, an ovoid shape, a gourd shape and a tear drop shape.

Figure 2:
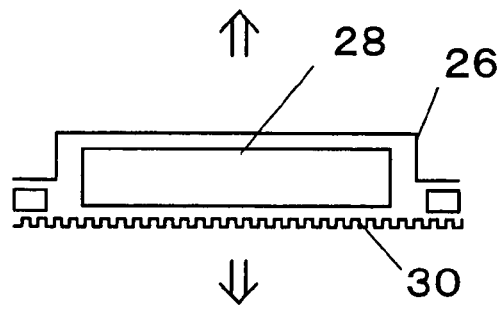
FIG. 2 is a cross-sectional view taken along line X1-X2 of FIG. 1.

FIG. 2 shows a schematic cross-sectional view taken along line X1-X2 of FIG. 1. The interlabial pad 10 comprises a liquid permeable surface side sheet 26 of the wearer's body side face 22 facing inner walls of labia; a permeable or non permeable back side sheet 30 facing the opposite side face 24 to the body side face, that is, the wearers clothing side; and an absorber 28. The interlabial pad 10 is an over-laid type pad, whose surface side sheet and back side sheet are bonded together at the outer edge of the absorbent. The surface side sheet 26 and the back side sheet 30 may be bonded by heat seal alone or in combination with a hot melt type adhesive. The interlabial pad 10 is not limited to the above-mentioned overlaid type structure, but may be an enclosing type structure composed of an absorber, and a water impermeable material positioned under an absorber, and a water permeable sheet covers the absorber and the water impermeable material entirely.

Next, a brief description of the surface side sheet and the absorber, which are main components of the interlabial pad will be given. A description of the back side sheet will be given later in relation to low friction characteristics.

Surface Side Sheet (Water Permeable Sheet)

It is preferable that the surface side sheet of the interlabial pad positioned at the body side is water permeable as described above. For the water permeable sheet, materials which are hydrophilic to liquid and non-irritant to the skin are used. By way of example, the following materials may be given: a nonwoven fabric or a combination thereof made with a melt blown method, a spun bond method, a point bond method, a through-air method, a needle punch method, a wet-type spun lace method, a foam film method, and so on.

Examples of fibrous sheets include sheeted fabrics which are any single or mixture of fibers made of rayon, acetate, cotton, pulp or synthetic resin, alone or a combination thereof so as to form a core- and-sheath structure.

Among the materials, considering the liquid mobility from the inner face of the labia, chemical stimulation by an activator, and contact state with the inner wall of the labia, it is preferable to apply spun-lace nonwoven fabric. It is prepared by the following procedures: Rayon with 1.1 to 4.4 dtex fineness and 7 to 51 mm fiber length is spread as a layer to have 40 to 80% of a specific weight per unit area to the total on the body face side. Mixtures of rayon with 1.1 to 4.4 dtex fineness and 7 to 51 mm fiber length and 14 to 42% of a specific weight per unit area to the total and PET with 1.1 to 4.4 dtex fineness and 7 to 51 mm fiber length and 6 to 18% of a specific weight per unit area to the total are spread as a layer on the garment face side. After laminating the two layers so as to make 20 to 60 g/m$^2$ of the total weight per unit area, the fibers are entangled by water-flow interlacing treatment and then dried to make spun lace nonwoven fabric with the thickness of 0.13 to 0.50 mm. During the above procedures, by mixing PET on the garment side face, bulkiness can be easily maintained even if the permeable sheet becomes wet. Therefore, the contact state between inner walls of the labia can be maintained.

Absorber

For the absorber contained in the interlabial pad, materials such as pulp, chemical pulp, rayon, acetate, natural cotton, super absorbent polymer, super absorbent polymer fiber and synthetic fiber, can be used independently or in a combination thereof. Mixtures of required compositions are formed into the absorber by known techniques such as pressing by an emboss former and entangling by needling, and as required, can be prepared by appropriately adjusting bulkiness, layering, folding or the like.

Sheet materials may be used after processed into sheets or powder, not being limited by the its application.

It is preferable for the absorber, although any material can be used as long as it is capable of absorbing and holding liquid (fluid), to be bulky, hard-to-be deformed, less chemically stimulant, and more preferably highly flexible to fit into the labia. Specifically, 50 to 150 g/m$^2$ of pulp with lengths thereof selected from the range of the fiber length of 1 to 10 mm is laminated on the garment side face. On the body side face, 150 to 250 g/m$^2$ of a mixture obtained by mixing 60 to 90% of rayon with 1.1 to 4.4 dtex fineness and 20 to 51 mm fiber length and 40 to 10% of natural cotton is laminated. The two laminated layers are formed into a sheet by a dotted emboss processor to have 2 to 10 mm bulkiness, and more preferable to have 3 to 5 mm bulkiness. Thereby, liquid can be easily transmitted from the body side face to the garment side face resulting in the improvement of the absorbing and holding capacity. Furthermore, by providing a mesh spun lace nonwoven fabric of rayon with 1.1 to 4.4 dtex fineness and 25 to 51 mm fiber length and a specific weight per unit area of 15 to 40 g/m$^2$, the liquid transmitted from the body side face can be dispersed by the mesh spun lace to be induced to almost all over the region of the pulp layer. Therefore, more liquid can be effectively absorbed.

Figure 3:
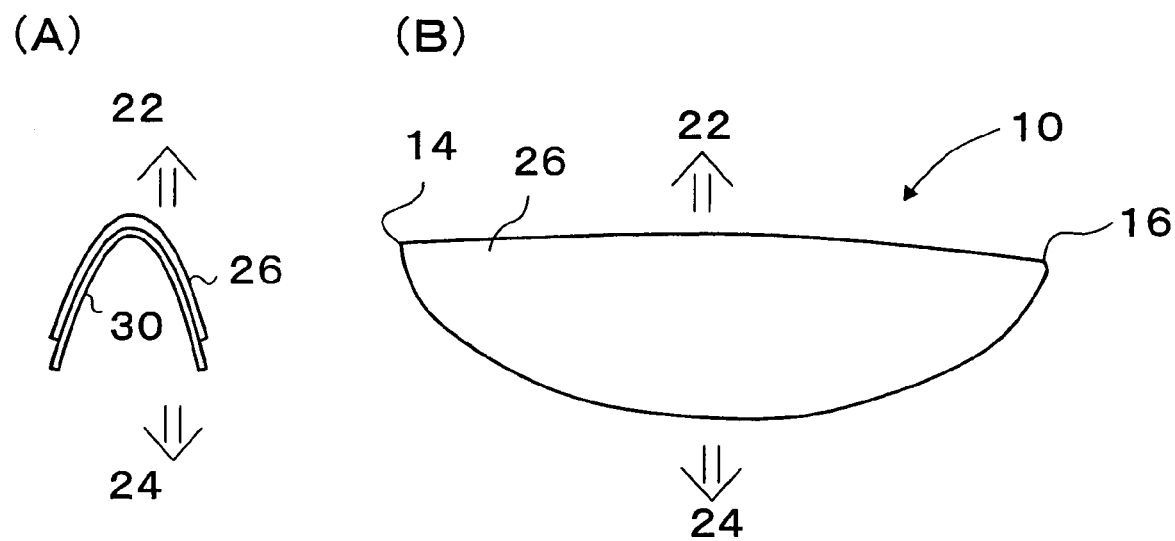
FIG. 3 shows an interlabial pad of the present embodiment. A front view of the folded interlabial pad is shown in (A). A side view of the pad seen from the left side is shown in (B).

The interlabial pad 10 shown in FIGS. 1 and 2 may be used being folded along the line from front 14 to rear 16 along the X-axis as shown in FIG. 3. Then, the surface side sheet 26 on the body side face 22 is facing the upper side (or outside). On the other hand, the opposite body side face 24 is facing the lower side and the back side sheet 30 is facing inside of the folded pad. In such structure, the surface side sheet 26 contacts the surface of the labia and the right and left sides of the pad contact the right and left sides of the labia respectively. Therefore, when the right and left sides of the labia move asymmetrically, the right and left sides of the interlabial pad can move to follow such movement of the right and left sides of the labia to some extent. That is, a sheet-like member can easily follow relatively the right and left phase shifts of the interlabial pad caused by body motions. In this case, however, the folded back side sheet slide against each other so that an object of the present invention is to reduce the friction produced under these conditions.

Back Side Sheet

Water Impermeability

As the materials for the water impermeable sheet which can be used for the back side sheet of the interlabial pad, materials which can prevent the menstrual blood contained in the absorber from leaking out of the interlabial pad can be used. Using the moisture-permeable materials may reduce the stuffy feeling so as to reduce the discomfort during use.

Examples of such materials include sheet films made of synthetic resins which are formed into membranes, breathing films made by drawing synthetic resin combined with inorganic fillers, laminated materials made by combining paper, nonwoven fabrics and films, and a gas-permeable and water non-permeable sheet having 10-30% of open pores and 0.1 to 0.6 mm diameter with capillaries disposed to extend toward the absorber.

Additionally, in considering flexibility so as not to degrade the wear feeling in use, a film having a weight per unit area of 15 to 30 g/m$^2$ and mainly comprising low density polyethylene (LDPE) resin which has a density of 0.900 to 0.925 g/cm$^3$ can be used as a preferred example. However, the combination or composition of the materials may vary to have the following low friction characteristics.

Low Friction Characteristics

On the garment side face of the back side sheet of the interlabial pad according to the present invention, the back side face has a surface structure hard to make an intimate contact with each other so as to reduce the friction force of the back side sheet against itself such that the interlabial pad can make right and left phase shifts easily. More concretely, reducing the ratio of contact area between top surfaces on one place and another place of the back side sheet may make it more difficult to make an intimate contact of mated surfaces. By way of example, it is also possible to make it less likely to make an intimate contact between the back side sheet and itself by applying lubricants such as silicone oil, polyhydric alcohol including glycerine and ethyleneglycol, paraffin wax and paraffin oil so that the back side sheet and itself are in contact under the presence of lubricants.

Combined Type of Laminated Fiber

Figure 4:
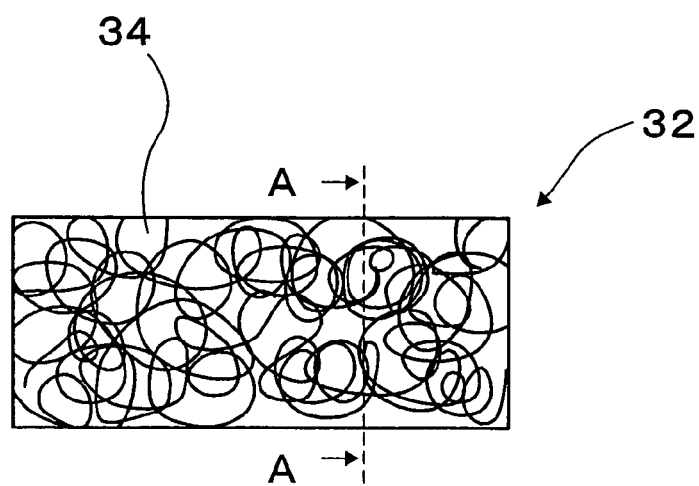
FIG. 4 is an enlarged plan view, seen from the bottom, of a part of the back side sheet of the interlabial pad having a laminated fiber composite according to an embodiment of the present invention.
Figure 5:
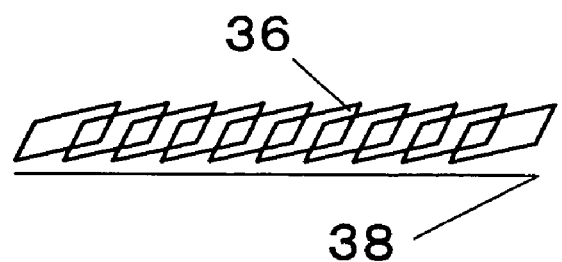
FIG. 5 is a cross-sectional view taken along line A-A of FIG. 4.

FIG. 4 shows a front view seen from the bottom of the back side sheet 32 made of a laminated fiber composite in a first embodiment. The unevenness formed by a laminated fiber composite 34 (FIG. 5) reduces the contact area at and between the top surface and itself of the folded back side sheet, consequently, reducing the close contact. Therefore, low friction will be achieved. As shown in FIG. 5, which is a cross-sectional view taken along line A-A of FIG. 4, the back side sheet 32 combined with the laminated fiber composite 34 was considered to tend to have high degree of stiffness, however, it is possible to give enough flexibility to the back side sheet by thinning a synthetic resin film into a resin film thin membrane or selecting an appropriate bonding method, therefore, the back side sheet 32 is suitable for the interlabial pad 10.

Particularly, in the embodiment shown in FIG. 5, a spun bond nonwoven fabric 36 is used as a fiber cluster forming the laminated fiber composite 34. A film 38 is made of polystyrene resin film 38.

Figure 6:
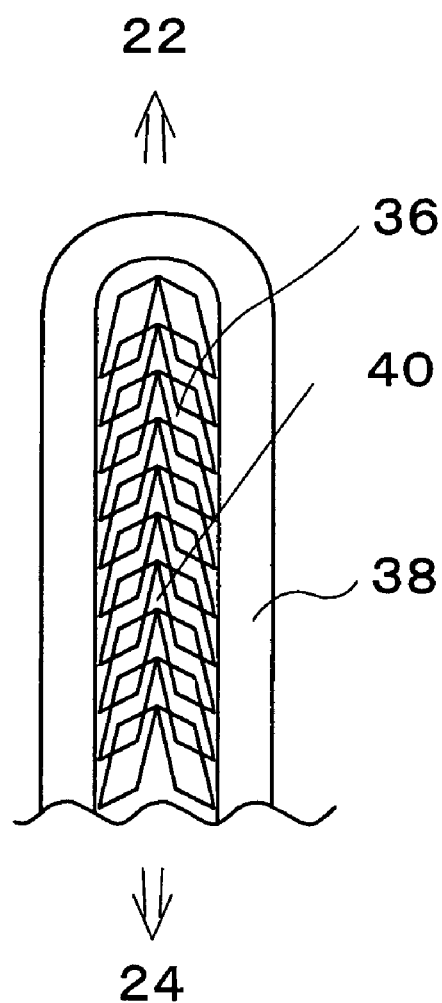
FIG. 6 is a cross-sectional view of a part of the folded interlabial pad having a laminated fiber composite according to an embodiment of the present invention.

FIG. 6 is a schematic diagram showing surfaces of one place and another of the back side sheet in contact with each other. As shown in FIG. 6, the surfaces not only have a small contact area but also gaps 40 are produced, therefore the moisture does not stay on the contact surface of the back side sheet even when the back side sheet becomes damp. Consequently, the friction will not change noticeably. Therefore, in either dry or wet conditions, the capability of the right and left sides of interlabial pad to follow the body motion will not change remarkably, which assures a quality of stability. For the resin film 38 of the present embodiment, a 22 g/m$^2$ film mainly composed of low density polyethylene having a density of 0.923 g/cm$^3$ and formed into a film by cast method is used.

As materials other than the above-mentioned films, sheet films made of synthetic resins such as PP and PET which are formed into membranes can be used. In considering flexibility so as not to degrade the wear feeling in use, it is preferable to use a film with a weight per unit area of 5 to 30 g/m$^2$ and mainly comprising low density polyethylene (LDPE) resin having a density of 0.900 to 0.925 g/cm$^3$. In addition, by drawing polyethylene resin with inorganic fillers such as calcium carbonate and barium sulfate, gaps are produced in the films to enhance the flexibility. As gas-permeability is also enhanced by this method, the hot and muggy feeling will be reduced, which will reduce the discomfort in use.

In the present embodiment, as the laminated fiber composite, a polypropylene spun bond nonwoven fabric having a weight per unit area of 20 g/m$^2$ and a fineness of 2.2 dtex is used. However, materials used as laminated fiber composites are not limited to a spun bond nonwoven fabric, but suitable fibers such as PP, PET, PP/PE, PET/PE (synthetic fibers with core-and-sheath structure) can be used. The preferred fineness of these fibers is 1.1 dtex to 6.6 dtex, more preferably, 1.7 dtex to 3.3 dtex. These laminated fiber composites are made by known methods such as spun bonding, spun lace, through air, and needle punch. The preferred weight per unit area of these laminated fiber composites is 15 to 50 g/m$^2$, more preferably, 18 to 25 g/m$^2$. Because materials in these ranges can be provided with gaps in order to reduce the number of contact points between top surfaces at one place and another place of the back side sheet in contact with each other, without degrading the flexibility and drape-feeling.

According to the present invention, the laminated fiber composite and the film are combined with a lamination method using a hot melt adhesive. However, the method is not limited to the lamination method, but other methods such as an extrusion lamination method applying thermoplastic resin to the laminated fiber composite can also be employed. To prevent the sheet from becoming stiffer and less flexible through this combining, it is preferable that the film and the laminated fiber composite are bonded partially. Because this may provide an interlabial pad with suitable flexibility and drape feeling as appropriate as the interlabial pad. More specifically, when bonded with a hot melt adhesive, the adhesive can be applied in dots, stripes, or spirals. When the film and the laminated fiber composite are bonded with the extension lamination method, they may be bonded with designed patterns on a chill roll such as a dot pattern and a rib-groove pattern.

Figure 7:
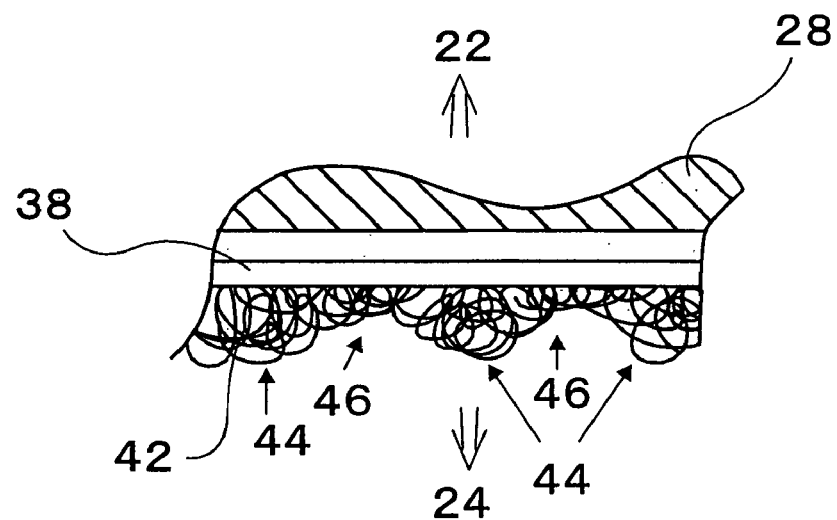
FIG. 7 is a cross-sectional view of a part of another interlabial pad having a laminated fiber composite according to an embodiment of the present invention.

FIG. 7 is a schematic diagram showing another embodiment using a laminated fiber composite. In this embodiment, the body side face 22 is the upper side, and the absorber 28, shown broken in this figure, is positioned on the side. The film 38 and the laminated fiber composite 42 are the same materials as used in the previous embodiment. The laminated fiber composite has protruding parts and recessed parts 46, which reduces the contact area. In addition, two contact surfaces may be kept a part appropriately because of the elasticity of the laminated fiber composite, which is considered to be effective for the reduction in the contact area and friction.

Figure 8:
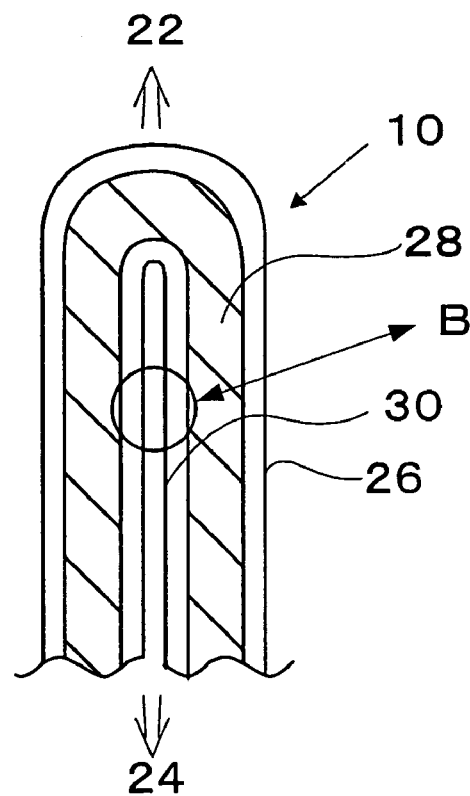
FIG. 8 is a cross-sectional view of a part of another folded interlabial pad having a fiber laminated body according to an embodiment of the present invention.
Figure 9:
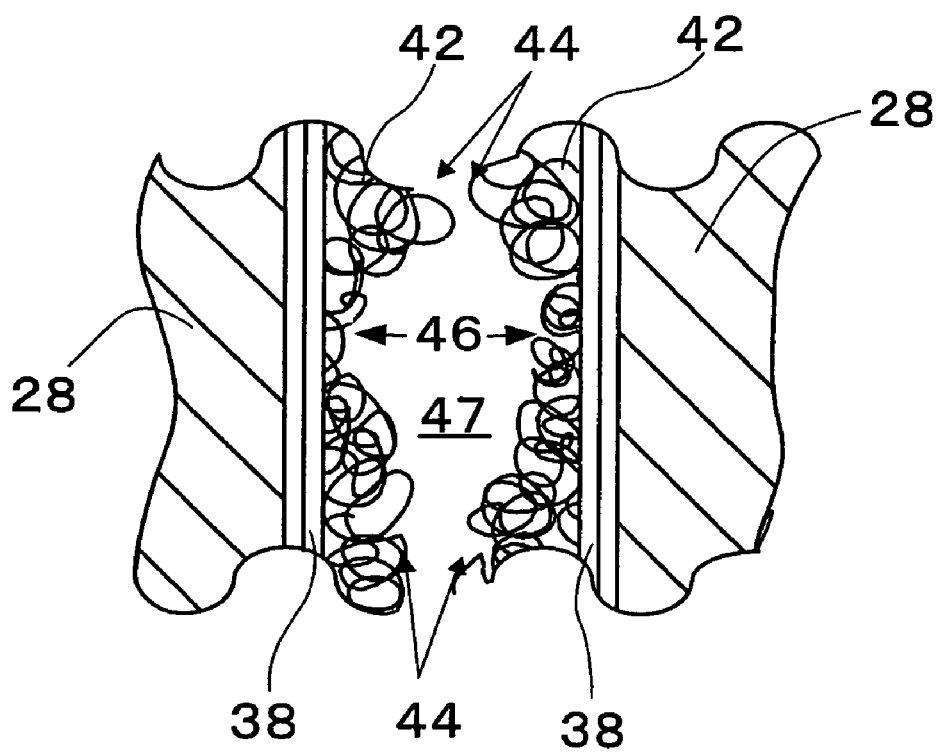
FIG. 9 is an enlarged partial view of portion B in FIG. 8

FIG. 8 shows a part of the interlabial pad 10 to which the back side sheet is applied. The absorber 28 is located between the surface side sheet 26 and the back side sheet 30 and though connected at the top part, the right and left parts of the absorber are separated by the back side sheet so that left and right absorbers can follow the motions of labia contacting the surface side sheet. FIG. 9 shows an enlarged view of B in FIG. 8. As in the case of FIG. 6, a gap 47 is produced by the recessed parts and protruding parts (46, 44) of the laminated fiber composite, which stabilizes and reduces the frictional coefficient.

Figure 10:
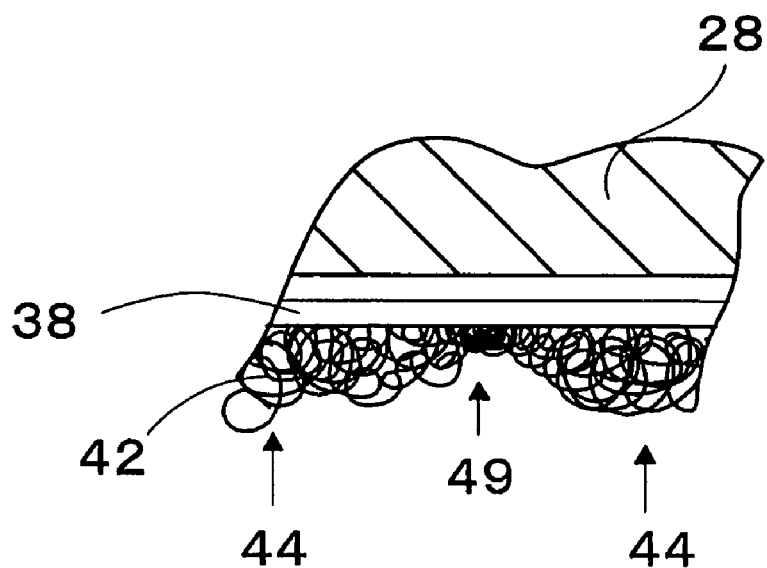
FIG. 10 is a cross-sectional view of a part of another interlabial pad having a laminated fiber composite according to an embodiment of the present invention.

FIG. 10 shows another embodiment. The laminated fiber composite 42 is also made of the same fiber and film as employed in the first embodiment. The composite 42 also has protruding portions 44. At the point corresponding to a recessed part, a melt-bonded zone 49 is made on the film using a hot melt adhesive. The above combination method may make desired protruding parts and recessed parts to form a low-friction shape.

Film Type Processed with Surface Protrusion and Recess

Figure 11:
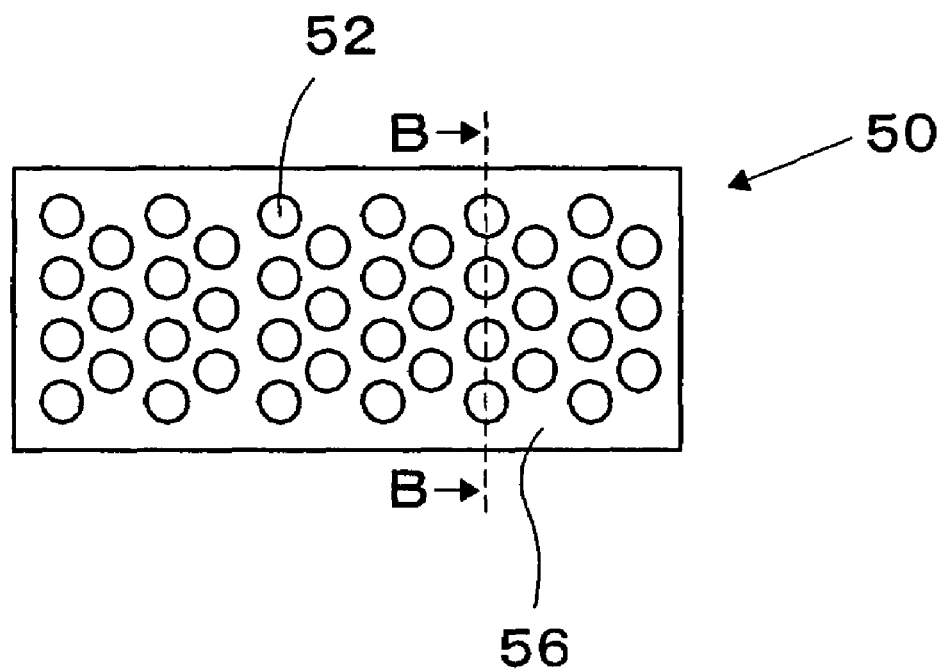
FIG. 11 is an enlarged plan view of a part of the back side sheet of the interlabial pad having an emboss portion, seen from the bottom according to an embodiment of the present invention.
Figure 12:
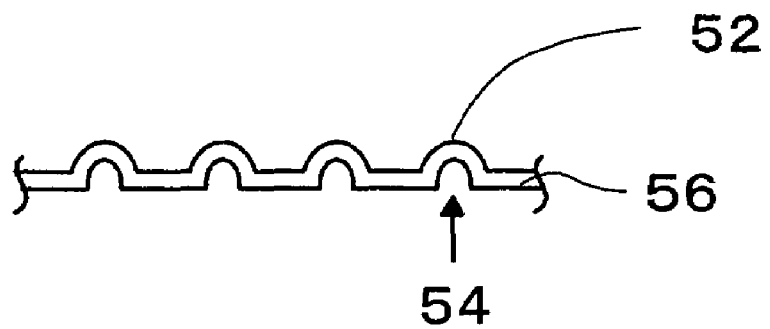
FIG. 12 is equivalent to the cross-sectional view taken along line B-B of FIG. 11. Two different cases are shown in (A) and (B), respectively
Figure 12:
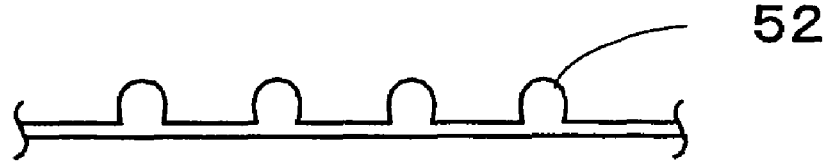

FIG. 11 is a front view of a back side sheet 50 of a fourth embodiment of the present invention. The back side sheet 50 includes the reference surface (or flat surface) 56 of the base member and a protrusion 52. The structure made of these multiple protruding portions reduces an intimate contact between surfaces at one place and another of the back side sheet. The resin material and emboss pattern of the back side sheet 50 can be selected considering the suitable flexibility for the interlabial pad. Such embodiments can be separated into the different two cases as shown in (A) and (B) in FIG. 12, (cross-sectional views taken along line B-B of FIG. 11). In (A) of FIG. 12, the back side sheet 50 having a recess 54 just behind each protrusion 52 is shown, as the protrusion 52 is made by pressing the film 56 with punch or the like to form the emboss surface. In (B) of FIG. 12 the back side sheet 50 having a protrusion 52 with a flat reverse side is shown.

Figure 13:
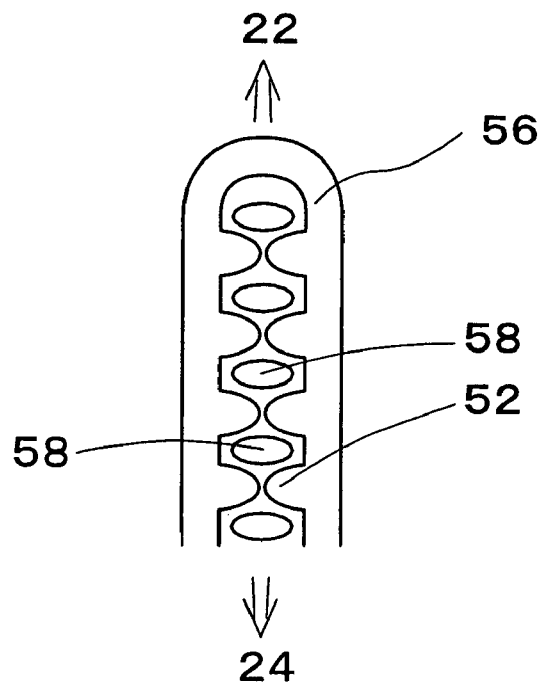
FIG. 13 is a cross-sectional view of a part of the folded interlabial pad having the emboss portion according to an embodiment of the present invention.

FIG. 13 is a schematic diagram showing a case of the back side sheet contacting itself. As gaps 58 are produced by the protrusions 52 of the film 56, even when the back side sheet becomes damp, the moisture does not stay on the contact surface of the back side sheet. Consequently, the friction will not change noticeably. The film 56 of the present embodiment is a polyethylene resin film. However, the material is not limited to this, but sheet films made of synthetic resins such as PP and PET, which are formed into membranes, can be used. In considering flexibility so as not to degrade the feel in use, it is preferable to use a film having a density of 0.900 to 0.925 g/cm$^3$. Filling inorganic fillers, such as calcium carbonate and barium sulfate, provides the film with minute pits and projections, which reduce the intimacy of contact. In addition, by drawing the film, pores may be introduced in the film, which reduce the stiffness. Also, as gas-permeability is generally obtained by this method, the hot and muggy feeling will be reduced, which will reduce the discomfort in use.

In the emboss processing of the present embodiment, the protrusion has a diameter of 0.2 mm at the top, a diameter of 0.6 mm at the bottom, and a height of 0.12 mm. The dots are placed in a 600 angle staggered arrangement with a pitch of 1.0 mm (Average embossing rate 5%). The emboss processing can be carried out in the following range, which is suitable for the interlabial pad. Preferably, the emboss rate is 1% to 50%, and more preferably, 1% to 30%. When the emboss rate is less than 1%, the emboss processing may produce no effect as the emboss area is too small to reduce the contact area between top surface and itself. On the other hand, when the emboss rate is more than 50%, not only the contact area between the top surface and itself may increase, but also the productivity of the emboss processing may be lowered.

Figure 14:
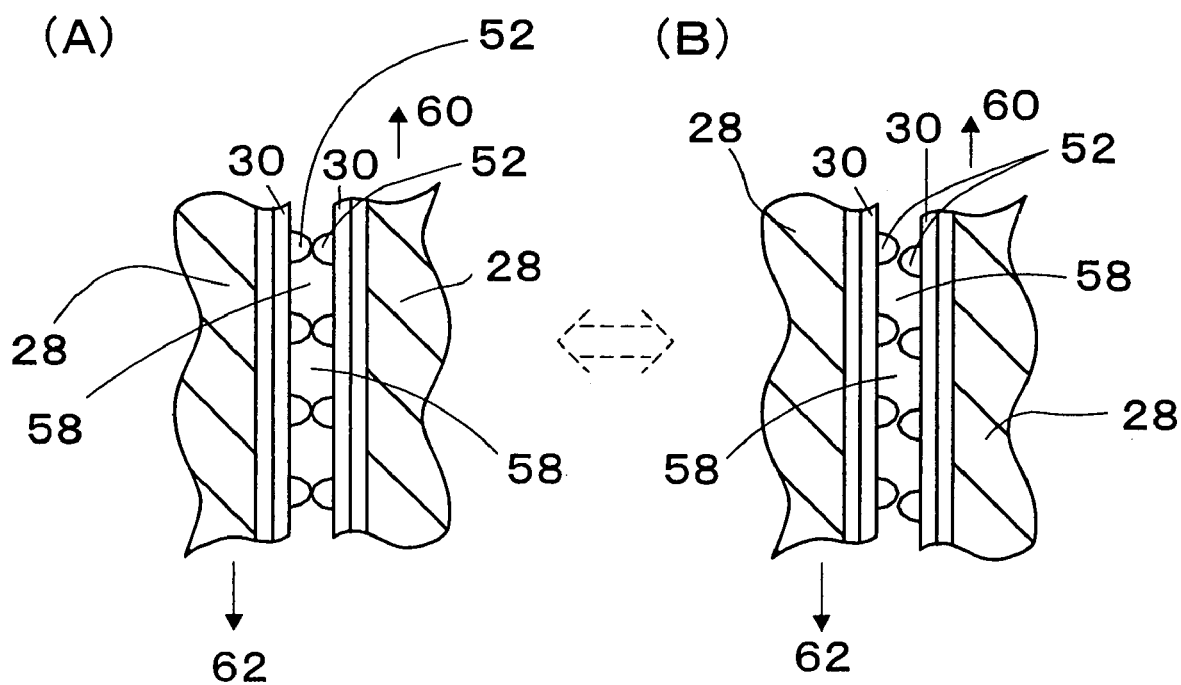
FIG. 14 shows a cross-sectional view (A) or (B) of a part of another folded interlabial pad having the emboss portion according to an embodiment of the present invention.

A schematic diagram of another embodiment of emboss processing is shown in (A) of FIG. 14. Similarly to FIG. 13, the case that the surfaces of the folded back side sheet 30 contact each other is described.

Figure 15:
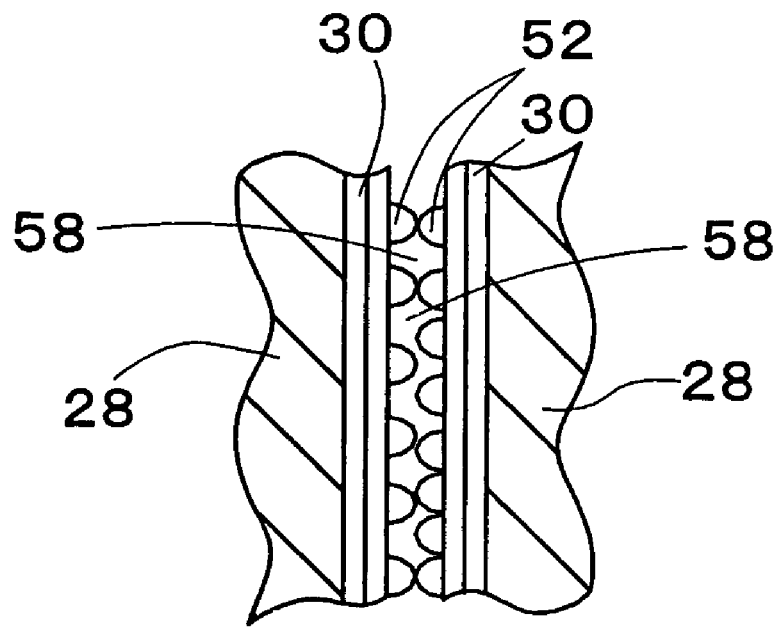
FIG. 15 is a cross-sectional view of a part of yet another folded interlabial pad having the embossing portion according to an embodiment of the present invention.

As the surfaces of the back side sheet 30, which are facing each other, come in contact near the top of each embossing portion (protrusion) 52, the contact area is small and the friction caused by sliding is low. In addition, gaps are produced between the part other than protrusions 58, which stabilizes the frictional coefficient as described above. Suppose the back side sheet part 30 shown in the right hand side slightly slides downward, and then upward pressure shown by an arrow 60 is applied to the right hand side sheet part while downward pressure shown by an arrow 62 is applied to the left side sheet part, the contact area is not large as the surfaces contact at the points a little below the top of the protrusions 52. However, the movement of the right and left sheet parts may cause each protrusion to catch its opposite protrusion, which may cause friction aside from the contact area. To avoid producing such friction by catching mechanically, it is recommended to adjust the pitch so that the protrusion parts may not catch each other in three dimensions. FIG. 15 shows this in two dimensions as an example. As the emboss portions facing each other are provided with different pitches, they will not catch each other as shown in (B) of FIG. 14. Thus, the friction can be reduced as a result of the reduced contact area.

Mini Sheet Piece

Figure 16:
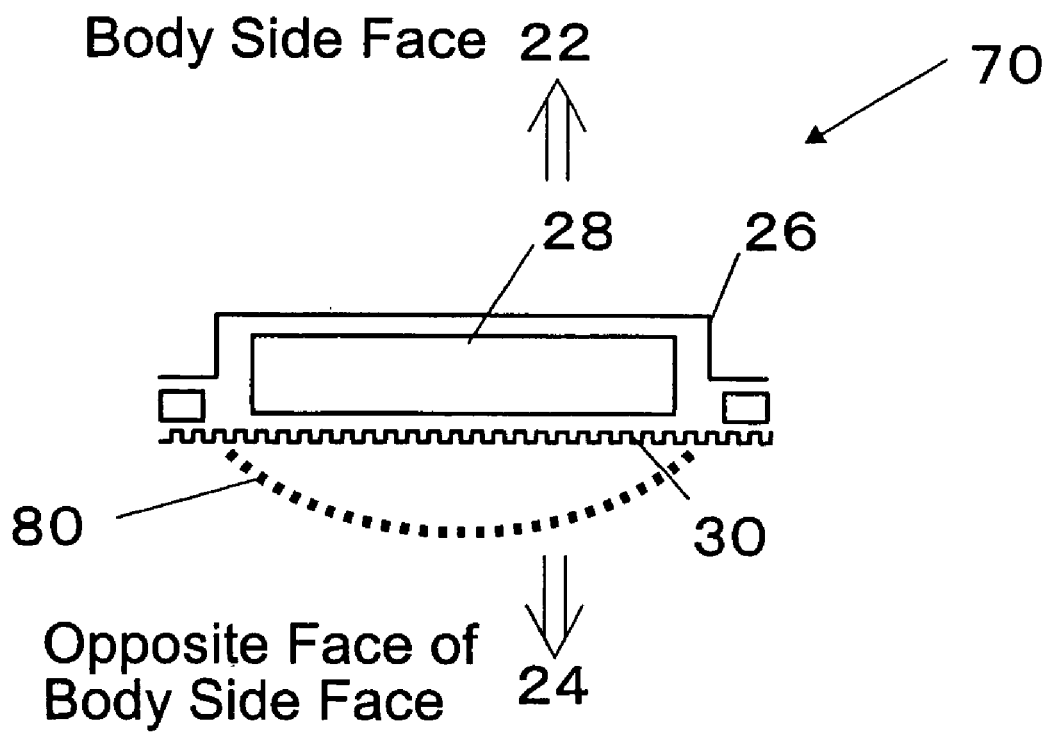
FIG. 16 is a cross-sectional view of the interlabial pad having a mini-sheet according to an embodiment of the present invention.

FIG. 16 shows one embodiment of the interlabial pad 70 having a mini sheet piece 80 fixed to a back side sheet in a cross-sectional view.

Similarly to the above-described embodiments, an absorber 28 is accommodated between the surface side sheet 26 facing the body side face 22 and the back side sheet 30. The mini sheet piece 80 can be attached to the back side sheet 30 by the means described above, such as hot melt adhesive, or other means.

The mini sheet piece can be attached to the side of the back side sheet facing the clothing extending astride both sides of the longitudinal center line, without interfering the right and left phase shifts of the interlabial pad. When the interlabial pad is worn by the wearer, the mini sheet piece prevents the close contact between the surfaces of the folded back side sheet by being placed between the folded back side sheet of the interlabial pad.

Also, it is preferable that the mini sheet piece is extensible so as not to interfere the right and left phase shifts of the interlabial pad.

Figure 17:
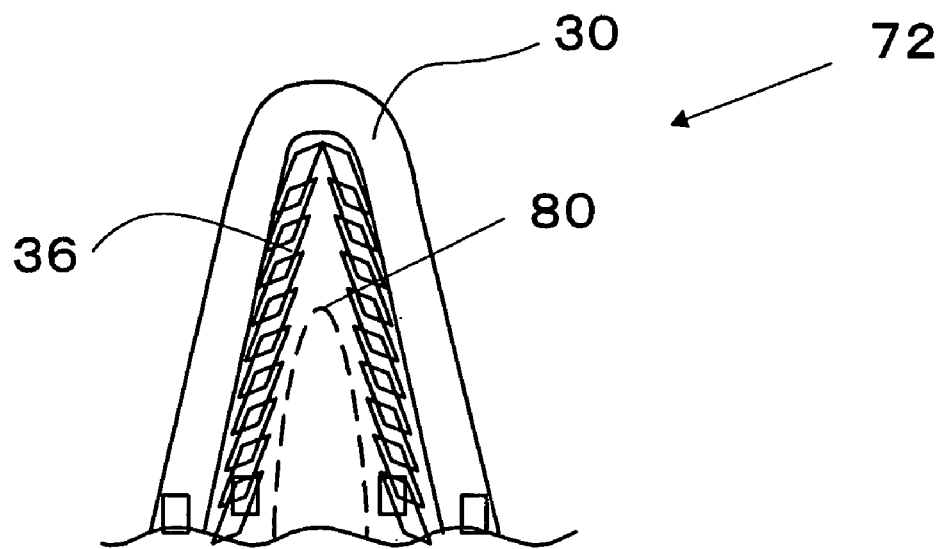
FIG. 17 is a cross-sectional view of a part of the folded interlabial pad having a mini-sheet and a back side sheet combined with a laminated fiber composite according to an embodiment of the present invention.

FIG. 17 is a schematic diagram of an interlabial pad 72, to which the mini sheet piece 80 is attached, according to another embodiment of the present invention. In this embodiment, the back side sheet 30 is made of the laminated fiber composite 36 and a film.

The materials are the same as the embodiments described above. In this embodiment, the mini sheet piece 80 is placed between the folded back side sheet 30. As this structure prevents the opposite surfaces of the folded back side sheet 30 from coming into direct contact with each other and increases the surface where the shear slide can occur, it is expected that the friction will be reduced still more.

Figure 18:
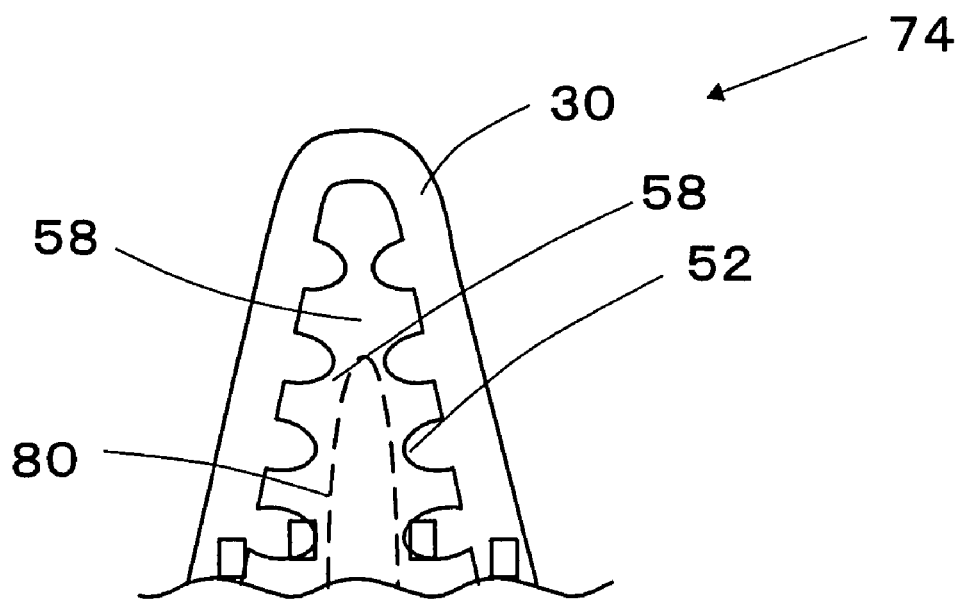
FIG. 18 is a cross-sectional view of a part of the interlabial pad having a mini-sheet and back side sheet with the embossing portion according to an embodiment of the present invention.

FIG. 18 is a schematic diagram of an interlabial pad 74, to which the mini sheet piece 80 is attached according to another embodiment of the present invention. In this embodiment, the back side sheet 30 with a plurality of emboss portions 52 is used.

The materials are the same as the embodiments described above. In this embodiment, the mini sheet piece 80 is placed between the folded back side sheet 30. As this structure prevents the opposite surfaces of the folded back side sheet 30 from coming into direct contact with each other and increases the surface where the shear slide can occur, it is expected that the friction will be reduced still more.

Figure 19:
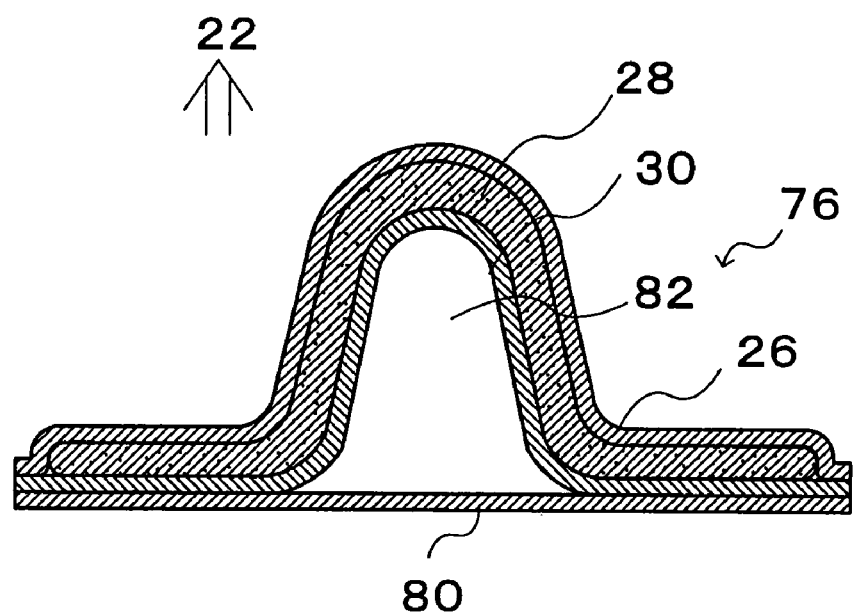
FIG. 19 is a cross-sectional view of another interlabial pad having a mini-sheet in an embodiment of the present invention.

FIG. 19 is a schematic diagram of an interlabial pad 76, to which the mini sheet piece 80 is attached, according to another embodiment of the present invention. A finger can be inserted into a space 82 surrounded by the back side sheet 30 and the mini sheet piece 80 to fit the pad.

In this embodiment, as the width of the mini sheet piece (breadthways length of the interlabial pad) is short, unlike the above-mentioned embodiments, the mini sheet piece does not necessarily separate folded-and-facing surfaces of the back side sheet 30 completely. Even in this case, as the back side sheet 30 has low friction shape of the present invention, the friction between the folded-and-facing surfaces of the back side sheet 30 is low.

Figure 20:
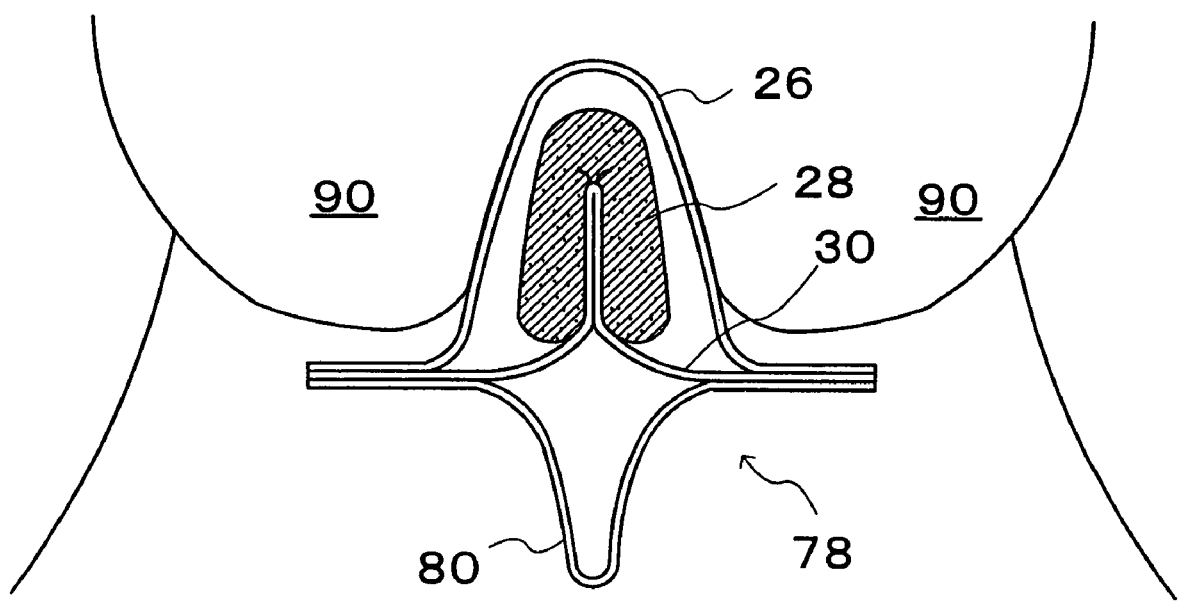
FIG. 20 is a cross-sectional view of another interlabial pad having a mini-sheet according to an embodiment of the present invention.

FIG. 20 shows a schematic diagram of an interlabial pad 78, being worn, to which the mini sheet piece 80 is attached, according to another embodiment of the present invention.

The mini sheet piece 80 is projected toward the opposite body side and does not have a strong influence on the friction. In this interlabial pad 78, the left side of the surface side sheet 26 contacts the left side of the labia and the right side of the surface side sheet 26 contacts the right side of the labia.

Therefore, when the left side of labia 90 moves forward (toward this side from the FIG. 20) and the right side of labia 90 moves backward (toward far side from the FIG. 20), the left side of the surface side sheet 26 moves forward and the right side of the labia moves backward, and in response to this movement, the left side of the absorber 28 moves forward and the right side of absorber 28 moves backward, and then, the left side of the back side sheet 30 moves forward and the right side of the back side sheet 30 moves backward.

As a result, friction between the folded-and-facing surfaces of the back side sheet 30 is produced to interfere the above movement. However, as the back side sheet 30 of the present invention has low friction, the back side sheet 30 slides against the opposite part of the folded back side sheet without interfering the movement of the labia.

Here, the method to wear the interlabial pads 76 and 78, which have the mini sheet piece, is briefly described with reference to FIGS. 19 and 20. As the interlabial pad 76 shown in FIG. 19 and the interlabial pad 78 shown in FIG. 20 are different in attaching each mini sheet piece, they can be different embodiments of the interlabial pads. However, with regard to the following description of the method to wear, the pads can be considered as the same pad.

The wearer can insert her finger into a pocket 82 formed by the back side sheet 30 and the mini sheet piece 80, from an opening of the pocket 82 of a finger insertion opening, with a fingerpring side of a part till the first joint of the finger (fingertip) contacting the opposite side face to the body side face of the back side sheet 30, so that she can hold the interlabial pad 76 or 78 on the fingertip.

When the finger is inserted into the pocket 82, the area with which the fingerprint side of the finger comes into contact has finger contact points which correspond to contact points suitable for locating the vaginal opening positioned deep inside the labia. The area including finger contact points comprises an area having the most suitable finger contact points for locating the vaginal opening, an area having suitable finger contact points, and an area having acceptable finger contact points. The finger insertion opening guides the inserted finger so that the fingerprint side of the fingertip may be brought to the area including the above-described finger contact points.

Thus, when guiding the interlabial pad 76 or 78 to the labia 90, with the contact point (not shown) located on the body side face of the interlabial pad 76 or 78 contacting the labia 90, by the medium of the absorber 28, by feeling the unevenness of the labia 90 with the finger cushion side of the fingertip inserted into the pocket 82, the interlabial pad 76 or 78 can be guided to the proper position in the labia 90, forming a concaved portion.

After putting the interlabial pad 76 or 78 into the labia 90 and pulling the finger out from the pocket 82, the mini sheet piece 80 hangs slack opposite to the body side face as shown in FIG. 20. Therefore, a used interlabial pad 1 can be removed by pulling the mini sheet piece 80. In addition, the mini sheet piece 80 made of non permeable or breathable material allows the wearer to pull and remove the interlabial pad 76 or 78 without soiling her fingers.

Generally, it is preferable to use extensible or elastic materials for the mini sheet piece 80. Because even if the wearer's finger is larger than the provided finger insertion opening, the mini sheet piece 80 stretches at least breadthways corresponding to the wearer's finger size, which allows the wearer to insert her finger and place the interlabial pad 76 or 78 properly although the wearer may have a large or small fingertip size.

Examples of materials essentially having elasticity include styrene-butadiene-styrene block copolymer (SBS), styrene-isoprene-styrene block copolymer (SIS), synthetic rubber such as urethane rubber, films made from amorphous olefin resin having a density of 0.88 to 0.900 g/cm$^3$, opening foam film and net. Woven fabrics or fabrics in which spun filaments made from synthetic rubber are interwoven can also be used. In addition, a spun bond nonwoven fabric, a melt blown nonwoven fabric and expanded foam sheet which mainly made from synthetic rubber can also be used.

In considering a soft feeling in use, a preferred example is a porous foam film opening foam film made from SEBS, adjusted to be 15 to 40μ thick and constructed to have pores of 0.28 to 1.77 mm$^2$ covering 40 to 70% of the total area.

Examples of nonwoven fabric include materials which mainly comprise heat shrinkable compound synthetic fibers having a high-melting core part and a low-melting sheath part, such as PE/PP, PE/PET, PP/PP; including a spun lace nonwoven fabric whose fibers are entangled by water streams, shrink-type nonwoven fabric whose fibers are shrunk by reheating air processing and so-called extensible spun bond, which is a sheet made from continuous long fiberby heat sealing and forced tentering in the longitudinal direction.

More specifically, a shrink-type nonwoven fabric which mainly comprises heat shrinkable compound synthetic fibers having a fineness of 1.1-4.4 dtex, a length of 7-51 mm, high-melting core part and low-melting sheath part, such as PE/PP, PE/PET, PP/PP and adjusted to have a weight per unit area of 10 to 60 μm$^2$ is a suitable material having a suitable softness and drape feeling. Laminated materials made of the materials described above can also be used.

When non-extensible materials processed to have extensibility are used, raw materials of combined synthetic fibers such as PE/PP, PE/PET, PP/PP, etc. which have thermal extensibility and composed of a core with high melting point material and a sheath with low melting point material formed from a thru-air nonwoven fabric being heat-treated by hot air and having bulkiness, a spun-lace fabric with entangled fibers by water stream pressure, a spun-bond nonwoven fabric made into sheet with laminated continuous fibers, a needle punch nonwoven fabric with entangled fibers by a needle, an SMS nonwoven fabric made into a sheet by multi-layering spun-bond and melt-blown fabrics, etc. and films mainly composed of PE resin, or a combination thereof may be used.

It is also possible to provide the above-described materials with extensibility using corrugate processing, in which the material is placed between male-female molds and embossed by heat, temperature and pressure. More specifically, the examples include a through air nonwoven fabric which mainly comprises compound synthetic fibers adjusted to have a fineness of 1.1 to 4.4 dtex and a weight per unit area of 10 to 60 g/m$^2$ and applied corrugate processing to have breadthways extensibility. Preferably, the male-female molds of the corrugate processing is arranged to achieve an extensibility at least 10%, and more preferably, to have an extensibility of 20 to 50%, yet more preferably, the processed material is extended by 30% with a load of 0.01 to 0.05 N/mm (Test condition: using tensilon tensile tester, velocity: 100 mm/min., chuck interval: 100 mm). For providing the materials with extensibility, methods such as making incisions or perforating can be used.

Hitherto, embodiments of the present invention using common materials have been described. In addition, the inventors have developed an interlabial pad which is also biodegradable, water dispersible and water-soluble. The description is as follows.

Structure of an Interlabial Pad Which is also Biodegradable, Water Dispersible and Water-Soluble It is more preferable hat the interlabial pad of the present invention comprises biodegradable and/or water dispersible and/or water-soluble materials. Such interlabial pads can be dropped into toilets and flushed away, which allows the easy and sanitary disposal of used pads and reduces the refuse in toilet facilities.

In this Specification, "biodegradable" means that a substance is decomposed into gas such as carbon dioxide or methane, water, and biomass under anaerobic or aerobic condition according to the natural process under the existence of bacteria represented by actinomycetes and other microbes, and also means that the biodegradability (biodegradable rate and biodegradable degree) of the substance equals to a material naturally generated such as fallen leaves or a synthetic polymer generally recognized having the same biodegradability under the same environment. "Water dispersible" has the same meaning as water diversifiable. It means a characteristic in which, while having no influence when used in a limited amount of moisture (menstrual blood), in a large amount of water or water current, the fabric is easily dispersed into small pieces at least to a degree where an ordinal toilet plumbing is not clogged. To be "water soluble" is to have a characteristic that, while having no influence when used in a limited amount of moisture (menstrual blood), the fabric is soluble in a large amount of water or water current.

Surface Side Sheet (Water Permeable Sheet)

As the materials for water permeable sheets, along with a spun lace nonwoven fabric, wet-process spun lacing nonwoven fabric selected from the nonwoven fabrics within a range of fiber length of 1 to 15 mm can be used. In addition to the above-described materials, resins which biodegrade by hydrolysis process, such as polylactic acid, polybutylene succinate can also be used. For example, a melt blown nonwoven fabric which is made from polylactic acid and adjusted to have a weight per unit area of 20 to 60 g/m$^2$ or a spun bond nonwoven fabric adjusted to have a weight per unit area of 15 to 30 g/m$^2$ and a fineness of 1.1 to 3.3 dtex can be used. For each nonwoven fabric material, aperturing is optional.

As another material, a synthetic or acetate fiber alone, or tow of continuous fiber of a laminated body may be used by adjusting a range of weight per unit area from 50 to 300 g/m$^2$ and by raveling fibers each other.

Moreover, among such materials, considering the hydrophilicity with the inner face of interlabia so as to be capable of preventing the wearer from feeling discomfort caused by slips between the interlabial pad and the surface of the labia, it is preferable to use wet-process spun lace nonwoven fabrics mainly comprising at least hydrophilic liquid fibers of cellulosic system.

Absorber

As the materials for absorbents, nonwoven fabric sheets made by needling can be used. Considering the biodegradability of polymer absorbents, it is preferable to use carboxymethyl cellulose fibers.

Back Side Sheet (Water Impermeable Sheet)

As materials for back side sheet (water impermeable sheet), PVA films, film sheets made by applying water-repellent processing on one side, both sides or some parts of PVA films using silicone and so on, PVA films mixed with silicone, starch films, laminated paper comprising films made of resins which biodegrade by hydrolysis process, such as polylactic acid and polybutylene succinate, and tissue. The materials may be colored by mixing inorganic pigments within a range of 0.1 to 5% as required.

When maintaining leakage prevention in humid conditions and avoiding an excessive load on septic tank is taken into consideration, a preferred material is laminated paper made by laminating a film made from polylactic acid to tissue having a thickness of 10 to 20µ and a weight per unit area of 15 to 20 g/m$^2$, with a bonded area of 5 to 40% of laminated area.

Laminated Fiber Composite

As materials for laminated fiber composites, a wet-process spun lace nonwoven fabric having a fiber length of 1 to 15 mm, along with a spun lace nonwoven fabric, can be used. In addition to the above-described materials, resins which biodegrade by hydrolysis process, such as polylactic acid, polybutylene succinate can also be used. For example, a melt blown nonwoven fabric which is made from polylactic acid and adjusted to have a weight per unit area of 20 to 60 g/m$^2$ or a spun bond nonwoven fabric adjusted to have a weight per unit area of 15 to 30 g/m$^2$ and a fineness of 1.1 to 3.3 dtex can be used.

Mini Sheet Piece

As materials for the mini sheet piece, films, a spun bond nonwoven fabric and a melt brown nonwoven fabric made from biodegradable resins, such as polylactic acid, polybutylene succinate; films and nonwoven fabrics made from water-soluble materials such as PVA and CMC; and water dispersible tissue and a spun lace nonwoven fabric mainly comprising cellulose fibers regenerated cellulose and others can be used.

It is preferable to use sheets of a spun bond nonwoven fabric or a melt blown nonwoven fabric, which mainly comprise biodegradable materials, are adjusted to have a fineness of 0.1 to 3.3 dtex and a weight per unit area of 15 to 40 g/m$^2$ and are subjected to the mechanical corrugate processing.

Figure 21:
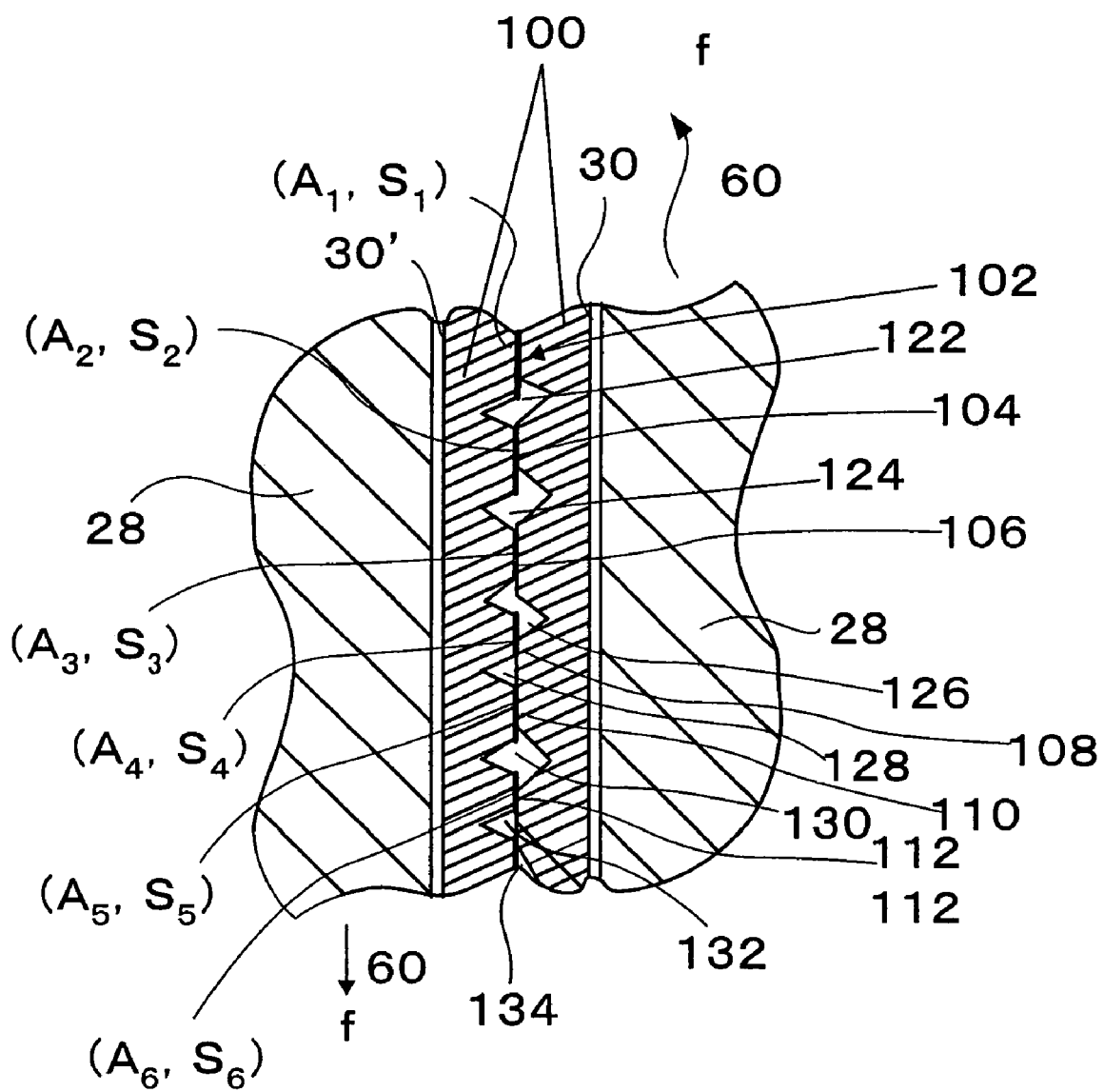
FIG. 21 is a drawing for the analysis of the low-friction mechanism. according to an embodiment of the present invention

FIG. 21 is intended for a schematic explanation about how reduced contact area reduces the friction. The explanation is attempted to explain experimental results. However, it is not needed that the following mechanism works out to reduce the friction according to the present invention.

The surfaces of the back side sheet 30, which are facing each other, have protruding and recesses parts 100, therefore, the surfaces do not contact over the whole area. The surfaces actually contact at point ($A_1$, $S_1$) 102, point ($A_2$, $S_2$) 104, point ($A_3$, $S_3$) 106, point ($A_4$, $S_4$) 108, point ($A_5$, $S_5$) 110 and point ($A_6$, $S_6$) 112; among these points, gaps 122, 124, 126, 128, 130 and 132 exist. Where $A_k$ is an actual contact area and $S_k$ is a shearing resisting strength per unit area of substances existing there (contaminants on the surface in many cases). Therefore, the frictional force f (60) caused by shearing such substances is $(A_1 \times S_1)+(A_2 \times S_2)+(A_3 \times S_3)+(A_4 \times S_4)+(A_5 \times S_5)+(A_6 \times S_6)$. As $S_k$ may be a physical property, which is usually considered to be constant, the frictional force f (60) is $S_k \times (A_1+A_2+A_3+A_4+A_5+A_6)$. As $(A_1+A_2+A_3+A_4+A_5+A_6)$ equals to the actual contact area between the back side sheet and itself, when this contact area is reduced, the friction will be reduced.

As is clear from the result of the embodiments and explanation above, it is preferable to use not only textures but also materials suitable for reducing friction between the two sliding surfaces. For example, synthetic resins including slidable polymer such as polytetrafluoroethylene and known self-lubricating materials can be used in forming low friction shape. By using proper lubricants, including solid and fluid lubricants, in addition to the reduction by shape, still more friction reducing effects are expected.

In the above, friction between the back side sheet and itself is described in detail. Friction between the back side sheet and other item, such as clothing, can be considered similarly. For example, for friction against underwear, it is similarly considered that a smaller contact area will make the friction smaller. Therefore, similar low friction shape can be considered.

INDUSTRIAL APPLICABILITY

As described above, according to the present invention, with respect to an interlabial pad which can make right and left phase shifts, if the back side sheet facing the garment side face has a structure and/or shape which less likely makes the intimate contact with the back side sheet itself, frictional resistance between the back side sheet and itself is decreased so that the interlabial pad can make right and left phase shifts easily. This can reduce the wearer's discomfort and it is unlikely that a friction force greater than the holding force of the labia to hold the interlabial pad applies to the back side sheet of the interlabial pad during the wearer's body motion.

By making a structure and/or shape which reduces the close contact of the surfaces of the folded back side sheet from laminated fiber composites and films, the points where the surfaces of the folded back side sheet contact each other will be reduced. Thus the frictional resistance will be reduced. Also, gaps are produced. Therefore, even when the back side sheet becomes damp, the moisture does not stay on the contact surface of the back side sheet, consequently, the frictional resistance will not change noticeably.

Employing the protrusion-recess processed surface structure (or protrusion processed surface structure), which makes less likely to have the close contact between the back side sheet and itself, the number of the contact points between the back side sheet and itself is reduced so as to reduce the frictional resistance. Also, gaps are produced so that even when the back side sheet becomes wet, moisture does not stay between the contacting surfaces of the back side sheet, and that the frictional resistance does not change noticeably. In addition, as the processing is applied secondarily, the manufacturing cost can be reduced.

In addition, when the mini sheet piece is attached to the side of the back side sheet facing the clothing extending astride both sides of the longitudinal centerline, without interfering the right and left phase shifts of the interlabial pad, in some cases, the mini sheet piece can prevent the intimate contact between the back side sheet and itself by being placed between the folded back side sheet when worn by the wearer.

According to the present invention, when an asymmetric motion, such as walking movement of the wearer, is made, a shearing force on right and left surfaces with regard to the longitudinal center line will be exerted on the interlabial pad supported between the labia. However, reducing the frictional resistance between the surfaces of the folded back side sheet facing the clothing will allow the interlabial pad to make right and left phase shifts easily.

Therefore, when the friction force between the surfaces of the folded back side sheet is smaller than the strength of the labia to hold the interlabial pad, the interlabial pad can follow the wearer's body motions, which will remarkably reduce the possibility that the interlabial pad may fall.

What is claimed is:

1. An interlabial pad which is folded along a longitudinal centerline to be worn by a wearer, the pad comprising:
   a body side face orientated toward a body side of the wearer;
   an opposite side face to the body side face facing an opposite body side and having
   a low friction shape with fine changes on each of first and second surfaces of the opposite side face, the first and second surfaces facing each other when said interlabial pad is folded along the longitudinal centerline, the low friction shape enabling a reduction in a resisting force when the first surface is sliding against the second surface to make right and left phase shifts when the interlabial pad is worn; and
   a mini sheet piece which is attached to the opposite side face of said interlabial pad, said mini sheet piece being extensible so as not to interfere with the right and left phase shifts of the first and second surfaces, wherein:
   the low friction shape includes at least one of:
   i) a film member formed by a laminated fiber composite that is combined with a resin, the laminated fiber composite providing an unevenness on each of the first and second surfaces, or
   ii) a film member formed by a laminated fiber composite that is combined with a resin, the film member being processed to provide protruding parts and receding parts of the film member on each of the first and second surfaces, the protruding parts being pitched to avoid catching among the protruding parts when the first surface is sliding against the second surface.

2. The interlabial pad according to claim 1, wherein the laminated fiber composite includes a nonwoven fabric having a weight of 15 to 50 $g/m^2$.

3. The interlabial pad according to claim 1, wherein the laminated fiber composite includes a nonwoven fabric having a weight of 18 to 25 $g/m^2$.

4. The interlabial pad according to claim 1, wherein the film member with protruding parts and receding parts has a density of 0.900 to 0.925 $g/cm^3$.

5. The interlabial pad according to claim 4, wherein the protruding parts and receding parts are embossed at an emboss rate of 1% to 50%.

6. The interlabial pad according to claim 4, wherein the protruding parts and receding parts are embossed at an emboss rate of 1% to 30%.

7. The interlabial pad according to claim 1, wherein said mini sheet piece is placed between the first arid second surfaces when the interlabial pad is folded.

8. The interlabial pad according to claim 1, wherein said mini sheet piece projects away from the opposite side face toward the opposite body side.

9. The interlabial pad according to claim 1, wherein a lubricant is applied to said opposite side face to the body side face.

10. The interlabial pad according to claim 1, wherein said interlabial pad is an interlabial pad for an incontinence.

11. The interlabial pad according to claim 1, wherein said interlabial pad is an interlabial pad for absorbing vaginal discharge.

12. An interlabial pad which is folded along a longitudinal centerline to be worn by a wearer, the pad comprising:
   a body side face orientated toward a body side of the wearer;

an opposite side face to the body side face facing an opposite body side and having a low friction shape with fine changes on each of first and second surfaces of the opposite side face, the first and second surfaces facing each other when said interlabial pad is folded along the longitudinal centerline, the low friction shape enabling a reduction in a resisting force when the first surface is sliding against the second surface to make right and left phase shifts when the interlabial pad is worn; and a mini sheet piece which is attached to the opposite side face of said interlabial pad, said mini sheet piece being extensible so as not to interfere with the right and left phase shifts of the first and second surfaces, wherein:

the low friction shape includes at least one of:
  i) a film member formed by a laminated fiber composite that is combined with a resin, the laminated fiber composite providing an unevenness on each of the first and second surfaces including a nonwoven fabric having a weight of 15 to 50 g/m², or
  ii) a film member formed by a laminated fiber composite that is combined with a resin, the film member being processed to provide protruding parts and receding parts of the film member on each of the first and second surfaces, the protruding parts being pitched to avoid catching among the protruding parts when the first surface is sliding against the second surface, the film member having a density of 0.900 to 0.925 g/cm³.

13. The interlabial pad according to claim 12, wherein the laminated fiber composite includes a nonwoven fabric having a weight of 18 to 25 g/m².

14. The interlabial pad according to claim 12, wherein the protruding parts and receding parts are embossed at an emboss rate of 1% to 50%.

15. The interlabial pad according to claim 12, wherein the protruding parts and receding parts are embossed at an emboss rate of 1% to 30%.

16. The interlabial pad according to claim 12, wherein said mini sheet piece is placed between the first and second surfaces when the interlabial pad is folded.

17. The interlabial pad according to claim 12, wherein said mini sheet piece projects away from the opposite side face toward the opposite body side.

* * * * *